United States Patent
Fortin et al.

(10) Patent No.: US 6,669,648 B1
(45) Date of Patent: Dec. 30, 2003

(54) CONTINUOUS NON-INVASIVE SPHYGMOMANOMETER

(75) Inventors: Jürgen Fortin, Graz (AT); Falko Skrabal, Graz (AT)

(73) Assignee: Cnsystems Medizintechnik GmbH, Graz (AT)

(*) Notice: Subject to any disclaimer, the term of this patent is extended or adjusted under 35 U.S.C. 154(b) by 0 days.

(21) Appl. No.: 09/937,826

(22) PCT Filed: Mar. 27, 2000

(86) PCT No.: PCT/AT00/00073
§ 371 (c)(1),
(2), (4) Date: Nov. 21, 2001

(87) PCT Pub. No.: WO00/59369
PCT Pub. Date: Oct. 12, 2000

(30) Foreign Application Priority Data

Mar. 30, 1999 (AT) .................................. 576/99

(51) Int. Cl.⁷ .................................. A61B 5/02
(52) U.S. Cl. ...................... 600/490; 600/485
(58) Field of Search ................. 600/490, 492, 600/493, 494, 495, 496, 498, 499, 481, 485

(56) References Cited

U.S. PATENT DOCUMENTS

| | | | |
|---|---|---|---|
| 4,406,289 A | 9/1983 | Wesseling et al. | |
| 4,510,940 A | 4/1985 | Wesseling | |
| 4,539,997 A | 9/1985 | Wesseling et al. | |
| 4,771,790 A | 9/1988 | Yamasawa et al. | |
| 4,850,369 A | 7/1989 | Yamasawa | |
| 4,862,895 A * | 9/1989 | Yamasawa et al. | 600/493 |
| 5,048,533 A * | 9/1991 | Muz | 600/492 |
| 5,651,370 A | 7/1997 | Hersh et al. | |
| 5,662,092 A | 9/1997 | Choi et al. | |

FOREIGN PATENT DOCUMENTS

| | | |
|---|---|---|
| AT | 391262 | 9/1990 |
| DE | 3829456 | 3/1990 |
| EP | 0395519 | 10/1990 |
| EP | 0426572 | 5/1991 |
| EP | 0537383 | 4/1993 |
| WO | 9422364 | 10/1994 |
| WO | 9500070 | 1/1995 |

* cited by examiner

*Primary Examiner*—Max F. Hindenburg
*Assistant Examiner*—Navin Natnithithadha
(74) *Attorney, Agent, or Firm*—Dykema Gossett PLLC

(57) ABSTRACT

According to the invention a sphygmomanometer for continuous plethysmographic measurement of blood pressure includes at least one inflatable pressure pad which is attachable to a body part containing an artery, arterial signal sensors for determining arterial blood flow, and a valve-controlled pressure chamber connected to a gas source and to the inflatable pressure pad and including a pressure sensor for measuring the pressure in the pressure chamber or in the pressure pad. The pressure chamber has separate inlet and outlet valves which are controlled dependent on signals of the arterial signal sensors.

31 Claims, 3 Drawing Sheets

Section A - A

CONTINUOUS NON-INVASIVE SPHYGMOMANOMETER

BACKGROUND OF THE INVENTION

In medicine there is a need to frequently, and possibly, continuously take blood pressure. Novel devices have been created In recent times for this purpose, The method devised by Panaz contributed an essential novelty (Digest of the 10$^{th}$ International Conference on Medical and Biological Engineering 1973 Dresden), wherein light is shone through a finger and the registered flow Is kept constant by a booster control.

This photoplethysmographic method was taken up by several others also (Yamakoshi, Wesseling, TNO). EP 537 383 (TNO) Apr. 21, 1993 (21.04.93) discloses an inflatable finger cuff used for non-invasive continuous monitoring of blood pressure. The inflatable cylindrical space is connected pneumatically to a fluid source. An infrared light source and a detector are positioned on both sides of the finger inside the fixed cylinder. A valve is provided for filling the cylinder with gas. Electrical cables for the infrared light source and the detector are threaded through. U.S. Pat. No. 4,510,940 A (WESSELING) Apr. 16, 1985 (16.04.85) and U.S. Pat. No. 4,539,997 A (WESSELING) Sep. 10, 1985 (10.09.85) disclose a device for continuous non-invasive measuring of blood pressure. A fluid-filled cuff, a light source, a light detector and a differential pressure booster are provided. U.S. Pat. No. 4,406,289 A (WESSELING) Sep. 27, 1983 (27.09.83) also discloses such a device according to the prior art.

The cited documents all show prior art only, especially so when it is considered that features essential to the invention are missing in the main claim.

A major problem of these methods is on the one hand in the cuffs being used which have to be placed very precisely, are very interference-prone and not very durable, and on the other hand is with the proportional valves used which are very expensive to manufacture (U.S. Pat. No. 4,406,289) and also in the calibrating of the device which can very precisely indicate the relative fluctuations in blood pressure, wherein absolute measuring however deviates considerably from the actual intra-arterial values. Usually, with the proportional valves used to date either a) a toggle flapper is used, which can be moved alternately in one or the other direction by an electromagnet, or b) an electromagnetic shaker is used. With both these proportional valves there is a constant gas flow through the pressure chamber, as there is a part of the valve always open. Either the outlet opening is released into the open, or the inlet opening is released by the gas supply. There is no position of the valves, in which both inlet and outlet opening are simultaneously closed.

This results in very high gas consumption, of little relevance in fixed apparatus, but clearly significant in the case of portable units. A further drawback is the use of pressure generation systems (usually pumps and compressors) which must generate a pressure flow without ripple, since any such ripple would influence the measuring signal. Pumps or compressors generating a constant and even air flow are generally more expensive and consume more power than pressure generation systems delivering a pressure which may not be under a specific threshold. The weight or the power consumption of the unit is clearly increased.

Yet another disadvantage of the methods utilised is that such methods used to date are employed exclusively on fingers, and the finger arteries belong to the small arteries which are regulated in the flow from the body for example by the temperature of the fingers, so that the pressure in these arteries no longer corresponds to the pressure in the large arteries, in which doctors are primarily interested. For this reason the devices used hitherto (for example the Finapres marketed by Ohmeda) very clearly give the relative fluctuations in blood pressure but not in absolute values of the pressure, so that the Finapres unit was also removed from the market.

Another existing sphygmomanometer essentially uses planartonometry. An array of very small pressure receivers, which are embedded in silicon, is applied to the artery by means of compressed air bellows, whereby a computer searches out the pressure sensor outputting the clearest signal. The pressure in the bellows is no longer altered after a clear signal has been found, while the pressure curve is calibrated by one-off or multiple measuring of the oscillometric blood pressure which can be measured intermittently on the same upper arm. When a hard object is applied, namely the array onto the artery, the former deforms in an uncontrollable manner, so that the pressure values output by this unit deviate very strongly from the intra-arterial values. (Zorn et al, Blood Pressure Monitoring 2: 185, 1997). Precise analysis of the pressure curves can additionally be employed by means of an expanded Windkessel model in known fashion to evaluate compliance of the large and small vessels, as demonstrated by Waft and Burrus. Furthermore, the pressure in the central aorta can also be calculated by computer, for example with frequency analyses, or a so-called augmentation index can also be calculated which clearly reflects the actual mechanical strain on the heart and vascular system. To date the so-called aplanation tonometry, wherein a hard pressure sensor was applied by hand or per micrometer screw to the artery, has been used to relieve arterial wall. The disadvantage of this so far has been that the pressure lying on the artery because of the pressure sensor was not known, and that it was exceedingly troublesome to accurately find the artery by hand.

The object of the present invention is to prevent these known difficulties by developing a new sphygmomanometer.

SUMMARY OF THE INVENTION

According to the invention a sphygmomanometer for continuous plethysmographic measurement of blood pressure includes at least one inflatable pressure pad which is attachable to a body part containing an artery, arterial signal sensors for determining arterial blood flow, and a valve-controlled pressure chamber connected to a gas source and to the inflatable pressure pad and including a pressure sensor for measuring the pressure in the pressure chamber or in the pressure pad. The pressure chamber has separate inlet and outlet valves which are controlled dependent on signals of the arterial signal sensors.

The sphygmomanometer according to the invention is described in greater detail with reference to the attached drawings.

DETAILED DESCRIPTION OF THE PREFERRED EMBODIMENTS

Figure 1:
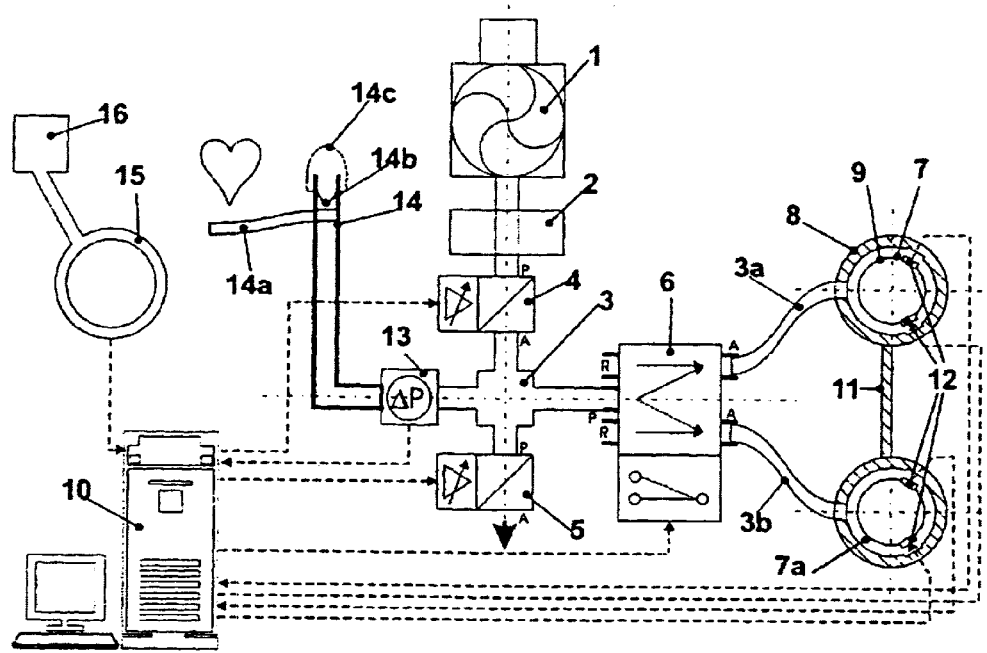
FIG. 1 shows the new blood pressure measuring system according to the invention.

In FIG. 1 the gas source is designated by reference numeral 1, which could refer to an air pump or also to a gas cartridge. An attenuator pad is designated by 2, for example a gas filter, which would equilise high-frequency irregularities of the gas supply, for example when a membrane pump is being used as a gas source and at the same time serves as dust filter. The pressure chamber is designated by 3, whereby the connection to gas source 1 is established by an inlet valve 4. The outlet valve is designated by 5. The valves could be conventional proportional valves, while the use of valves with very short response times is particularly beneficial, as given for example by piezoelectric elements. Response times for these piezoelectric valves of around a millisecond can give rise to pressure changes here which can be in a frequency range of up to 50 Hz. With the use of piezoelectric valves the valves can be controlled digitally and especially easily by a computer 10, so that characteristics can be imparted to the valves by way of this digital control, not attainable or only with difficulty so with conventional proportional valves or with forced coupling of outlet and inlet valve (such as for example in U.S. Pat. No. 4,406,289 Wesseling). Each desired pressure cycle can thus be adjusted in pressure chamber 3 with an upper limit frequency of ~50 Hz and gas consumption can also be kept low.

Pressure chamber 3 can be connected via another reversing valve 6 for example with two or more pressure pads 7 by way of lines 3a and 3b of pressure chamber 3, which serve as artery compression. If only one pressure pad is used reversing valve 6 can be omitted. The relatively rigid outer wall is designated by 8. Its purpose is to keep the compliance of pressure pad 7 low. Reference numeral 9 designates a mouldable membrane which serves as artery compression. In a special case pressure pads 7 are distinguished as annular in cross-section, because they are designed for use on fingers, by which pressure pad 7 is attached. Reference numeral 11 designates a rigid positioning component, by means of which both pressure pads 7 can be connected. The advantage here is that the position of pressure pads 7 on the fingers is guaranteed in relatively constant alignment. A constant position of arterial signal sensors 12 applied to the limit of pressure pads 7 relative to the artery lying beneath mouldable membrane 9 is guaranteed. With arterial signal sensors 12 it could be a matter of, for example, light sources and light sensors (arterial signal receivers 12a and arterial signal senders 12b) which measure the flow of the artery, or also ultrasound sensors or lasers or even pressure sensors. Therefore, controlled by arterial signal receivers 12, which are likewise attached to computer 10, the desired pressure can be produced any time in pressure pad 7. Instead of pressure pads 7 illustrated here as annular in shape, any other shape adapted to the body part in use could be used in this instance. Should the sphygmomanometer be used for example on the skull above the arteria temporalis, flat pressure pads 7 would be suitable.

Moreover, anywhere in the vicinity of the communicating interstice, formed by pressure chamber 3 and pressure pad 7, a pressure sensor 13 is attached which measures the pressure in the pressure chamber and forwards the results to computer 10. The pressure measured in the pressure chamber with appropriate control by means of arterial signal sensors 12 corresponds to the arterial pressure. By way of advantage with the illustrated pressure sensor 13 it could well be a matter of a differential pressure sensors. The advantage of this would be that pressure measuring can be corrected any time to the artery height difference, relative to the heart. For this a fluid-filled line would have to be available which reaches the level of the heart (symbolically illustrated in FIG. 1 with a heart). By way of advantage fluid-filled line 14 is filled with a fluid which corresponds to the density of blood. The fluid, with which line 14 is filled, should exhibit a slight output coefficient (for example oily fluids). The hose can be attached by means of a fastening mechanism 14a (such as a locking band, pressure knob, clamp and the like) to the extremity (for example upper arm or article of clothing) at heart level. A free-floating membrane 14b, which prevents the fluid from escaping, but which allows the fluid column to move, could be attached at the heart end of line 14. Another air-permeable but hard-wearing membrane 14c or a fine-mesh grille 14c, which prevents free-floating membrane 14b from being damaged, could be attached via free-floating membrane 14b.

Another pressure pad 15 can also be added, which comes to rest via another artery, preferably a major artery, which can be connected to another gas source 16 to measure the blood pressure there conventionally, for example oscillometrically or auscultatorically. In the same way and with adequate capacity gas source 1 could be used, effectively necessitating more valves (not illustrated). It is known that conventional blood pressure measuring, such as auscultatoric or oscillometric measuring, works intermittently, that is, normally at intervals of minimum half a minute to a minute. The other pressure pad is likewise connected to computer 10, so that calculation and display of the continuous arterial pressure, as determined in the small artery by pressure pad 7, is automatically corrected to the true value of the blood pressure in the major artery, as is measured by pressure pad 15.

The added advantage of the second pressure measuring via a major artery by pressure pad 15: for continuous measuring of pressure by pressure pad 7 the pressure in pressure pad 7 must constantly track the average arterial pressure, that is, the operating point must be readjusted. To readjust the operating point the continuous blood pressure measuring must be briefly interrupted by pressure pad 7. Major changes in the average arterial pressure can now be discovered by measuring pressure in another artery by pressure pad 15 discontinuously, and the operating point can be continually adapted automatically and without interruption to the continuous measuring of pressure by pressure pad 7. In this way continuous, unbroken recording of the true intra-arterial pressure curve is possible using the above-described sphygmomanometer. By changing automatically from one pressure pad 7 to the other pressure pad 7a via reversing valve 6 measuring of pressure is not interrupted, since the patient does not experience any discomfort from continuous measuring on the same spot.

Figure 2:
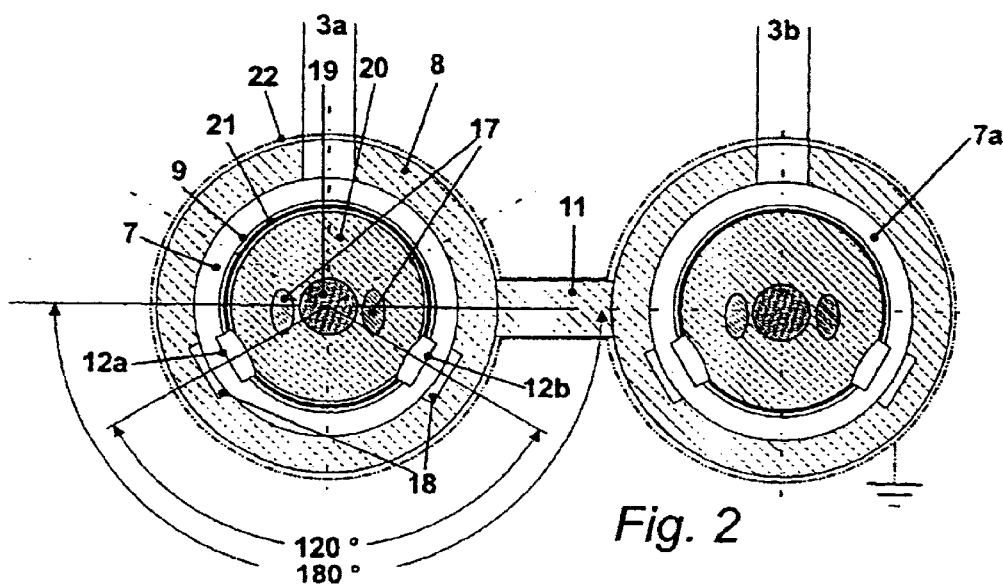
FIG. 2 shows the new finger cuff in greater detail.

FIG. 2 illustrates an advantageous embodiment of pressure pad 7 which comprises a relatively rigid outer wall 8 which on the one hand gives pressure pad 7 beneficial minimal compliance, and on the other hand allows rigid connection 11 to adjacent pressure pad 7a which is designed similarly. Located inside relatively rigid outer wall 8 is mouldable membrane 9, on which in the illustrated case arterial signal sensors 12 rest. There is thus no interfering membrane between arterial signal receivers (flow sensors) 12 and arteries 17 which might impair measurement of the blood flow. As mentioned, these flow sensors could be LED's combined with light detectors, (for example photodiodes), lasers (or laser diodes) and photodiodes or ultrasound emitters and receivers (arterial signal receivers 12a and arterial signal receivers 12b). Using other pressure sensors (see FIG. 3) is also feasible. Recesses 18, into which arterial signal sensors 12 can disappear, are realised advantageously in the relatively rigid outer wall for arterial signal sensors 12 when mouldable membrane 9 is close to rigid outer wall 8. This close fit is accordingly meaningful to keep the compliance of pressure pad 7 to a minimum. In the illustrated example two arterial signal receivers 12a and 12b are attached to one another at an angle of 120° to ensure an optimum signal, arteries 17 lie relative to finger bone 19 in finger 20, corresponding to an angle of 180° in illustrated pressure pad 7, and the clearest signal is emitted, when arterial signal receivers 12a and arterial signal receivers 12b are positioned at ca. 120° to one another, as already mentioned, since at the same time an even better and more homogeneous pressure can be exerted on the artery. This is therefore the case because then only mouldable membrane 9, and not arterial signal receivers 12a and 12b, which are not mouldable, which comes to rest on artery 17.

In the illustrated example mouldable membrane 9 consists of gas-tight and fluid-tight synthetic material. In order to make measuring more pleasant for the patient, a skin-friendly tissue 21 is additionally applied between mouldable membrane 9 and the body, which for example could comprise nylon or other synthetic tissues, cotton or similar. In the process the skin-friendly tissue releases arterial signal receivers 12a and 12b, so that the signal is not impaired. Of particular benefit are those materials which can readily be cleaned or disinfected. Electrical shielding 22 is also provided which keeps electrical interference away from arterial signal receivers 12. In the illustrated example electrical shielding 22 is applied externally on rigid outer wall 8, but could also be placed inside rigid outer wall 8.

To ensure correct positioning of arterial signal sensors 12 above artery 17, if only one pressure pad 7 is present, it can be beneficial to also mount rigid positioning component 11 on rigid outer wall 8, if only one pressure pad is used. Rigid positioning component 11 is then formed to the adjacent body structures (in the case of a finger for example the adjoining fingers, back of hand, palm; in the case of the thumb the ball of the thumb, not illustrated) and could thus also take on a ring shape or form parts of a ring.

Figure 3:
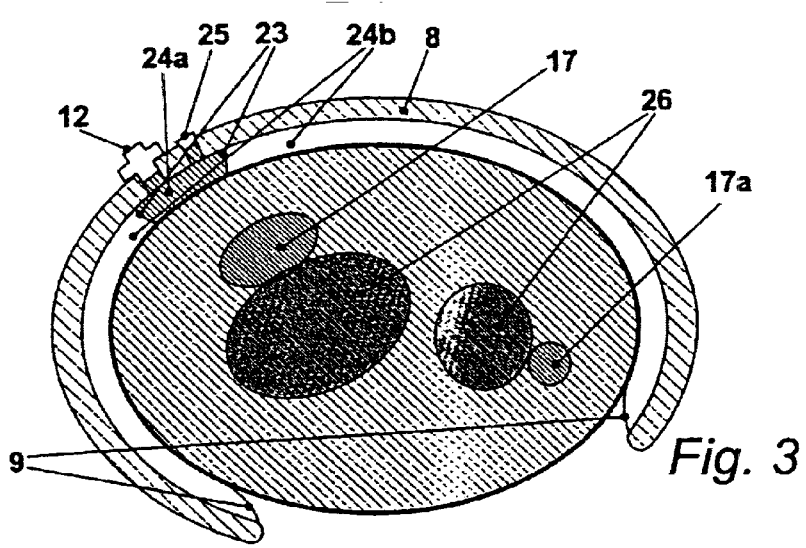
FIG. 3 illustrates an embodiment of the blood pressure measuring system, wherein pressure sensors are used as arterial signal sensors

As illustrated in FIG. 3, it can be beneficial to mount pressure sensors as arterial signal sensors 12 in rigid outer wall 8. In this illustrated example it can be beneficial to divide the communicating system, comprising pressure chamber 3 and pressure pad 7, by additional easily mouldable septums 23 which create separate areas 24a and 24b in the pressure chamber. Area 24a located in the vicinity of the arterial signal receivers could then be filled with another medium, namely with fluid, to better transmit the signals emitted by the artery to the arterial signal receivers. Reference numeral 25 designates a filling or ventilating aperture which can be sealed and which is located in relatively rigid outer wall 8, by way of which sector 24a can be filled with a fluid. The advantage of this embodiment is that in the concrete example arterial signal sensor 12 can also be a high-resolution pressure receiver which can absorb the pure, unattenuated signals from artery 17 lying on bone 26, without impairing these mechanically. In this way the continuous pulse curve can be recorded ongoing in high resolution, while a precisely known pressure of artery 17 can be applied via flexible septums 23. The arterial wall can thus be relieved, and a pure pulse curve can be recorded continuously.

In the embodiment used here blood pressure can be measured using pressure sensor 13, which is connected to sector 24b of pressure pad 7, also oscillometrically in known fashion, and then with knowledge of the systolic, diastolic and average arterial pressure, any desired pressure in relation to the systolic, diastolic and average arterial pressure in pressure pad 7 and thus also in fluid-filled area 24a can be created in order to thus record the pulse curve with precisely defined pressure ratios and thus to enable continuous bloodless recording of blood pressure. It is understood that other arterial signal sensors 12 (receiver 12a and sender 12b), as for example light-sensitive sensors and LED's can be installed in the rigid outer wall.

Figure 4:
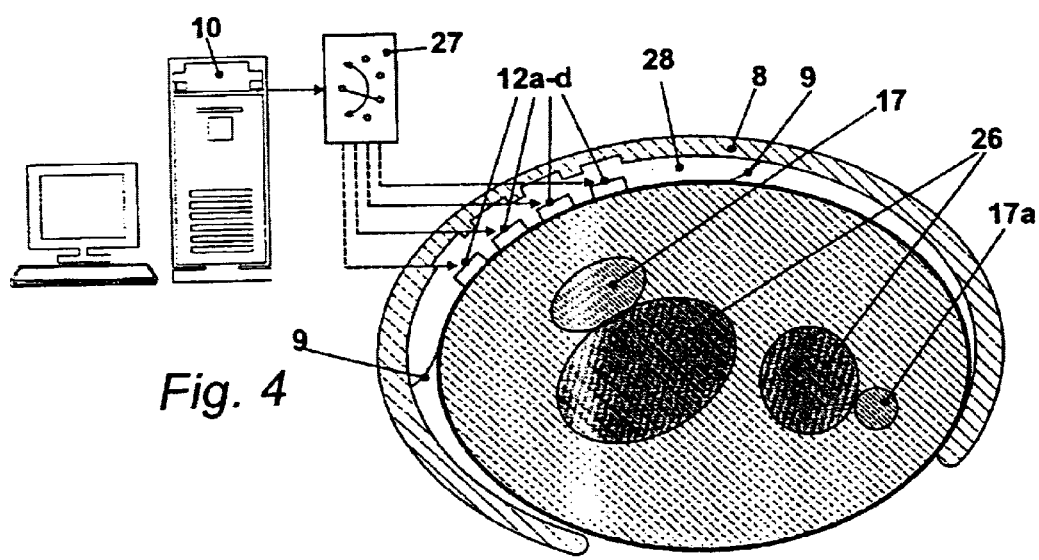
FIG. 4 illustrates an embodiment of the blood pressure measuring system, wherein several signal sensors are used as arterial signal receivers.

As illustrated in FIG. 4, several arterial signal receivers (12a–d) may be present, whereby a multiplex switch 27 and computer 10 carry out the choice of the optimally placed arterial signal receivers 12a–d in order to receive an optimum arterial signal. This is particularly beneficial for enabling interference-free recording of signals when the artery is in a position altered from individual to individual. It would be ideal, instead of localizing pressure pad 7 above a small artery, for example the finger artery, with the necessity of recalibrating the measuring by another pressure pad 15 which lies above a large artery, to utilise just one pressure pad 7 from now on over a major artery, which allows continuous measuring of pressure and at the same time the absolute values can be correctly determined. An example of such an artery is the arteria radialis or temporalis, which is on the one hand large enough to be representative of the major arteries, but on the other hand still allows recording of arterial signals, such as flow metering by irradiation or reflection on underlying bone 26 (for example, the radius or skull bones) by waves emitted to arterial signal senders 12b. The additional advantage of the arteria radialis for example is that yet another artery, namely other artery 17a in this instance the arteria ulnaris, is available. For measuring only artery 17 has to be compressed by pressure pad 7, and not other artery 17a and the blood flow to the extremity is consequently not interrupted. In addition, only mouldable membrane 9 has to be inflatably connected to a sector 28 of rigid outer wall 8 in that area which lies above artery 17 being examined, while other artery 17a is not compressed by mouldable membrane 9.

Figure 5:
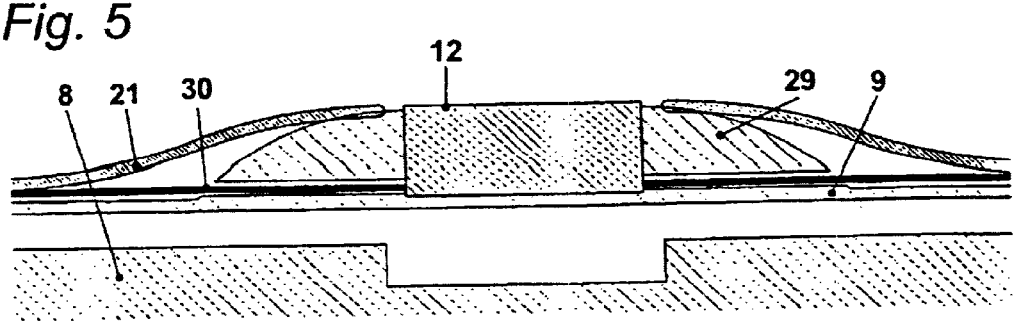
FIGS. 5, 6 and 7 are detailed illustrations of the arterial signal receivers.

FIG. 5 illustrates a practical realisation of the device, as it is advantageous if the arterial signal receivers (receiver 12a and sender 12b) are supported on mouldable membrane 9. In this case the mouldable membrane, which may comprise latex, for example, is not interrupted, rather arterial signal sensor 12 is cast in a mouldable lens 29, preferably from the same material as mouldable membrane 9, which is attached to membrane 9 (for example stuck or vulcanised). At the same time electrical wires 30 are guided between mouldable membrane 9 and skin-friendly tissue 21, so that these wires can also be guided to computer 10 while shielded mechanically and insulated.

Figure 6:
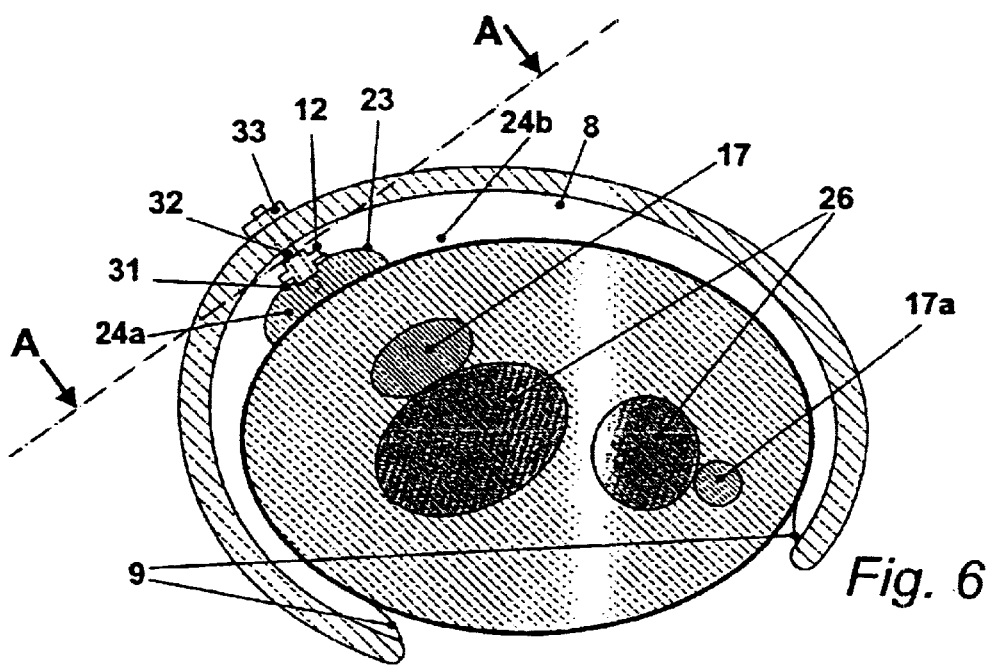

FIG. 6 illustrates another embodiment of the planned device, wherein arterial signal sensors 12 are applied to a strip 31, whereby strip 31 represents a part of septum 23 which separates gas-filled area 24b from fluid-filled area 24a. Gas-filled area 24b is drawn through on the side turned away from the body, so that when the pressure in pressure chamber 3 is raised (and thus in gas-filled area 24a) the arterial signal receivers cannot or can only slightly alter their position to artery 17 and in any case cannot be lifted from the body. An optimum signal is always obtained from arterial signal sensors 12 independently of the pressure in pressure chamber 3. So that arterial signal sensors 12 in strip 31 cannot tilt, an additional one, preferably two stayers 32 are solidly connected to strip 31, and are mounted movably in relatively rigid outer wall 8, in guide openings 33, for example. And so that optimum pressure transmission without loss of pressure from area 24b to area 24a is possible, strip 31 is narrow so that septum 23 can transmit the pressure from area 24b to area 24a from several sides.

Figure 7:
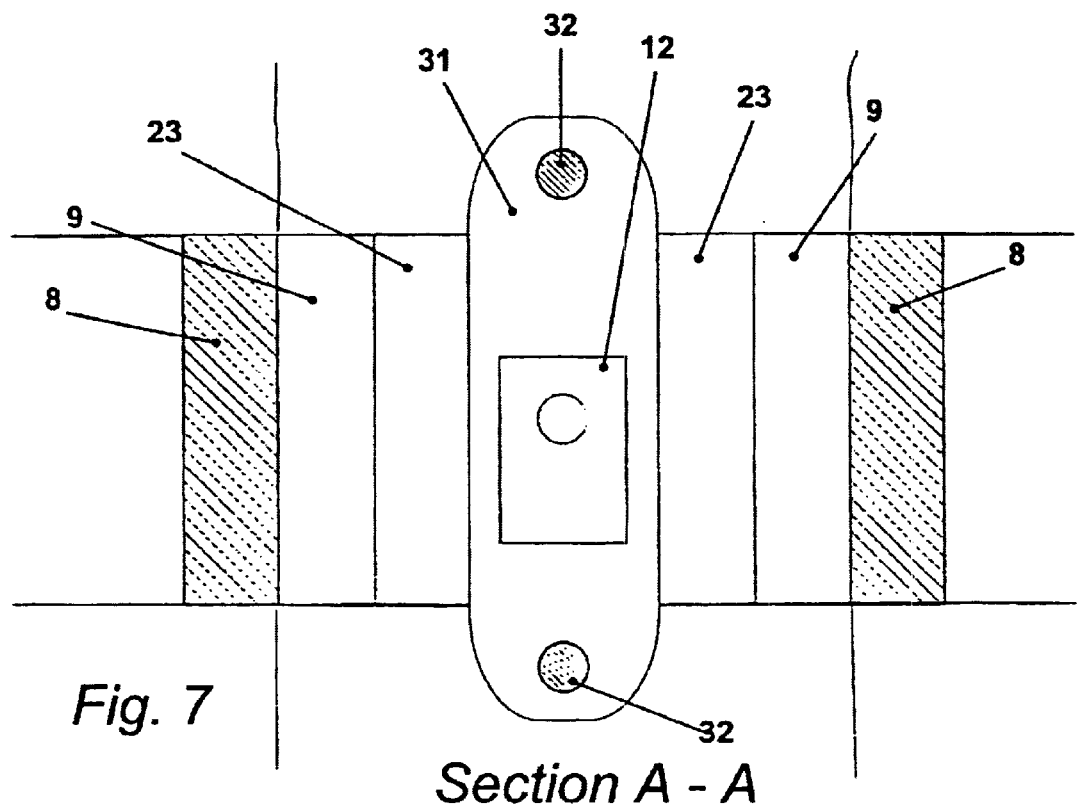

As FIG. 7 illustrates stayers 32 are passed by outside gas-filled area 24b of pressure pad 7 so that pressure pad 7 does not have to be interrupted.

| Legend | |
|---|---|
| 1 | gas source |
| 2 | attenuator |
| 3 | pressure chamber |
| 4 | inlet valve |
| 5 | outlet valve |
| 6 | reversing valve |
| 7 | pressure pad |
| 8 | rigid outer wall |
| 9 | mouldable membrane |
| 10 | computer |
| 11 | rigid positioning component |
| 12 | arterial signal sensors |
| 12a | arterial signal receiver |
| 12b | arterial signal sender |
| 13 | pressure sensor |
| 14 | fluid-filled line |
| 14a | fastening device |
| 14b | easily mouldable floating membrane |
| 14c | hard-wearing, air-permeable membrane |
| 15 | other pressure pad |
| 16 | additional gas source |
| 17 | artery |
| 17 | another artery |
| 18 | depressions |
| 19 | finger bones |
| 20 | finger |
| 21 | skin-friendly tissue |
| 22 | electrical shielding |
| 23 | septums |
| 24a | 24b separate areas |
| 25 | ventilating apertures |
| 26 | bones |
| 27 | multiplex switch |
| 28 | outer wall sector |
| 29 | mouldable lens |
| 30 | electrical wires |
| 31 | strip |
| 32 | stayer |
| 33 | guide openings |

What is claimed is:

1. A sphygmomanometer for continuous plethysmographic measurement of blood pressure, comprising:
   at least one inflatable pressure pad which is attachable to a body part containing an artery;
   arterial signal sensors for determining arterial blood flow;
   a valve-controlled pressure chamber connected to a gas source and to the inflatable pressure pad, having a pressure sensor for measuring the pressure in the pressure chamber or in the pressure pad; and
   a computer, with valve control of the pressure chamber dependent on signals of the arterial signal sensors;
   wherein the pressure chamber is fitted respectively with a separate inlet and outlet valves.

2. A sphygmomanometer as claimed in claim 1, wherein an arterial signal receiver and an arterial signal sender are machined into a mouldable membrane of said pressure pad and wherein in a rigid outer wall of the pressure pad is available, containing depressions for the arterial signal sensor.

3. A sphygmomanometer as claimed in claim 1, wherein the pressure pad is annular in shape.

4. A sphygmomanometer as claimed in claim 1, wherein the pressure pad exhibits a rigid outer wall with at least one rigid positioning component.

5. A sphygmomanometer as claimed in claim 4, wherein the rigid positioning component presents a ring or parts of a ring.

6. A sphygmomanometer as claimed in claim 5, wherein an additional pressure pad is located in an additional ring of the positioning component, and wherein a reversing valve is arranged upstream of the pressure chamber with which the pressure pads can be impacted with pressure alternately.

7. A sphygmomanometer as claimed in claim 1, wherein a further pressure pad is provided on another body part with an artery for conventional, intermittent, oscillatory or auscultatoric measuring of blood pressure, with the operating point for continuous measuring of blood pressure being regulatable by said further pressure pad.

8. A sphygmomanometer as claimed in claim 7, wherein the computer continuously standardizes the continually measured blood pressure to the blood pressure measured intermittently said further pressure pad.

9. A sphygmomanometer as claimed in claim 1, wherein several arterial signal sensors are provided, from which the computer searches out and controls the arterial signal sensor(s) with the best signal characteristic.

10. A sphygmomanometer as claimed in claim 1, wherein only one sector of a rigid outer wall of the pressure pad, containing the arterial signal sensors, is lined with a mouldable membrane.

11. A sphygmomanometer as claimed in claim 1, wherein the arterial signal sensors are applied at an angle of about 120° to one another.

12. A sphygmomanometer as claimed in claim 1, wherein the pressure sensor of the pressure chamber is a differential pressure sensor, whose one part is connected to the interior of the pressure chamber or to the pressure pad and whose other part is connected to a fluid-filled line.

13. A sphygmomanometer as claimed in claim 12, wherein the fluid-filled line is filled with a liquid of low vapor tension.

14. A sphygmomanometer as claimed in claim 13, wherein the fluid-filled line is sealed at its side facing away from the differential pressure sensor with a deformable membrane.

15. A sphygmomanometer as claimed in claim 14, wherein the deformable membrane is surrounded on its outside by a rigid, air-permeable membrane.

16. A sphygmomanometer as claimed in claim 12, wherein the fluid-filled line is fitted with a fastening device on its heart end.

17. A sphygmomanometer as claimed in claim 1, wherein a gas cartridge is used as gas source.

18. A sphygmomanometer for continuous plethysmographic measurement of blood pressure, comprising:
   at least one inflatable pressure pad which is attachable to a body part containing an artery;
   arterial signal sensors for determining arterial blood flow;
   a valve-controlled pressure chamber connected to a gas source and to the inflatable pressure pad, having a pressure sensor for measuring the pressure in the pressure chamber or in the pressure pad; and a computer, with valve control of the pressure chamber dependent on signals of the arterial signal sensors;

wherein at least one arterial signal sensor is machined into the side of the pressure pad facing away from the body; and wherein the pressure pad is separated by at least one mouldable septum into separate areas, which areas are filled with different media, for example gas or fluid, with at least one arterial signal sensor being assigned to one of the separate areas.

19. A sphygmomanometer as claimed in claim 18, wherein the arterial signal sensors are taken up in the side of the mouldable septum facing away from the body.

20. A sphygmomanometer as claimed in claim 19, wherein the arterial signal sensors are arranged on a strip.

21. A sphygmomanometer as claimed in claim 20, wherein the strip is mounted movably opposite a rigid outer wall of the pressure pad.

22. A sphygmomanometer as claimed in claim 21, wherein the strip has stayers which are guided movably in guide opening in the rigid outer wall of the pressure pad.

23. A sphygmomanometer as claimed in claim 3, wherein the pressure pad is annular in shape.

24. A sphygmomanometer as claimed in claim 3, wherein a further pressure pad is provided on another body part with an artery for conventional, intermittent, oscillatory of auscultatoric measuring of blood pressure, with the operating point for continuous measuring of blood pressure being regulatable by said further pressure pad.

25. A sphygmomanometer as claimed in claim 3, wherein only one sector of a rigid outer wall of the pressure pad, containing the arterial signal sensors, is lined with a mouldable membrane.

26. A sphygmomanometer as claimed in claim 3, wherein a gas cartridge is used as gas source.

27. A sphygmomanometer as claimed in claim 3, wherein the arterial signal sensors are mounted in a mouldable lens and wherein all electrical connections are guided to the arterial signal sensors outside of the pressure pad and inside a skin-compatible tissue.

28. A sphygmomanometer for continuous plethysmographic measurement of blood pressure, comprising:

at least one inflatable pressure pad which is attachable to a body part containing an artery;

arterial signal sensors for determining arterial blood flow;

a valve-controlled pressure chamber connected to a gas source and to the inflatable pressure pad, having a pressure sensor for measuring the pressure in the pressure chamber or in the pressure pad; and a computer with valve control of the pressure chamber dependent on signals of the arterial signal sensors;

wherein the pressure chamber comprises a separate inlet valve and a separate outlet valve; and wherein several arterial signal sensors are provided, from which the computer searches out and controls the arterial signal sensor(s) with the best signal characteristic.

29. A sphygmomanometer for continuous plethysmographic measurement of blood pressure, comprising:

at least one inflatable pressure pad which is attachable to a body part containing an artery;

arterial signal sensors for determining arterial blood flow;

a valve-controlled pressure chamber connected to a gas source and to the inflatable pressure pad, having a pressure sensor for measuring the pressure in the pressure chamber or in the pressure pad; and a computer, with valve control of the pressure chamber dependent on signals of the arterial signal sensors;

wherein the pressure chamber comprises a separate inlet valve and a separate outlet valve; and wherein only one sector of a rigid outer wall of the pressure pad, containing the arterial signal sensors, is lined with a mouldable membrane.

30. A sphygmomanometer for continuous plethysmographic measurement of blood pressure, comprising:

at least one inflatable pressure pad which is attachable to a body part containing an artery;

arterial signal sensors for determining arterial blood flow;

a valve-controlled pressure chamber connected to a gas source and to the inflatable pressure pad, having a pressure sensor for measuring the pressure in the pressure chamber or in the pressure pad; and a computer, with valve control of the pressure chamber dependent on signals of the arterial signal sensors;

wherein the pressure chamber comprises a separate inlet valve and a separate outlet valve; and wherein the arterial signal sensors are applied at an angle of about 120° to one another.

31. A sphygmomanometer for continuous plethysmographic measurement of blood pressure, comprising:

at least one inflatable pressure pad which is attachable to a body part containing an artery;

arterial signal sensors for determining arterial blood flow;

a valve-controlled pressure chamber connected to a gas source and to the inflatable pressure pad, having a pressure sensor for measuring the pressure in the pressure chamber or in the pressure pad; and a computer, with valve control of the pressure chamber dependent on signals of the arterial signal sensors;

wherein the pressure chamber comprises a separate inlet valve and a separate outlet valve; and wherein the pressure sensor of the pressure chamber is a differential pressure sensor, whose one part is connected to the interior of the pressure chamber or to the pressure pad and whose other part is connected to a fluid-filled line.

\* \* \* \* \*